(12) United States Patent
Blake et al.

(10) Patent No.: US 7,678,574 B2
(45) Date of Patent: Mar. 16, 2010

(54) SENSITIVITY CONTROLS FOR BLOOD SEROLOGY PREPARED FROM MODIFIED CELLS

(75) Inventors: Deborah Adella Blake, Auckland (NZ); Lissa Gwyneth Gilliver, Auckland (NZ); Stephen Michael Henry, Howick (NZ); Ji Chen, Auckland (NZ)

(73) Assignee: KIWI Ingenuity Limited, Auckland (NZ)

(*) Notice: Subject to any disclaimer, the term of this patent is extended or adjusted under 35 U.S.C. 154(b) by 884 days.

(21) Appl. No.: 10/492,863

(22) PCT Filed: Oct. 16, 2002

(86) PCT No.: PCT/NZ02/00214

§ 371 (c)(1),
(2), (4) Date: Oct. 22, 2004

(87) PCT Pub. No.: WO03/034074

PCT Pub. Date: Apr. 24, 2003

(65) Prior Publication Data

US 2005/0042697 A1 Feb. 24, 2005

(30) Foreign Application Priority Data

Oct. 16, 2001 (NZ) .................................. 514849
Jan. 29, 2002 (NZ) .................................. 516901

(51) Int. Cl.
*G01N 31/00* (2006.01)
(52) U.S. Cl. .................. 436/8; 435/2; 435/40.5; 435/326; 435/372; 435/375; 436/17; 436/513; 436/519; 436/520; 436/521; 436/63; 436/166; 436/174; 422/61
(58) Field of Classification Search ............... 435/7.21, 435/7.25, 7.5, 377, 285.2, 287.2, 288.3, 290.2, 435/7.1, 7.92–7.95, 961, 962, 971, 973, 2, 435/40.5, 326, 372, 375; 436/506, 513, 519, 436/520, 529, 533, 546, 15, 17, 63, 166, 436/174, 517, 523, 524, 528, 535, 538, 548, 436/172, 811, 819, 521; 422/61
See application file for complete search history.

(56) References Cited

U.S. PATENT DOCUMENTS 4,609,627 A * 9/1986 Goldstein .................. 435/269
5,512,485 A 4/1996 Young et al.
5,677,176 A 10/1997 Nicolau et al.
6,440,736 B1 * 8/2002 Logtenberg et al. ......... 435/375

FOREIGN PATENT DOCUMENTS

| JP | 2001089484 | 4/2001 |
|---|---|---|
| WO | WO 00/23570 | 4/2000 |
| WO | WO 01/49825 | 7/2001 |

OTHER PUBLICATIONS

Mouneimne et al., Electroinsertion of xeno proteins in red blood cell membranes yields a long lived protein carrier in circulation, Biochimica et Biophysica Acta 1066: 83-89 (1991).*
Civenni et al., In vitro Incorporation of GPI-Anchored Proteins Into Human Erythrocytes and Their Fate in the Membrane, Blood 91(5): 1784-1792 (1998).*
Tolvanen et al., In vitro Attachment of Mono- and Oligosaccharides to Surface Glycoconjugates of Intact Cells, The Journal of Biological Chemistry 261 (20): 9546-9551 (1986).*
Mouneimne Y. et al., "Electroinsertion of Xeno Proteins in Red Blood Cell Membranes Yields a Long Lived Protein Carrier in Circulation" Biochimica et Biophysica Acta, vol. 1066, pp. 83-89, 1991.
Civenni G. et al., "In Vitro Incorporation of GPI-Anchored Proteins Into Human Erythrocytes and Their Fate in the Membrane", Blood, vol. 91, No. 5, pp. 1784-1792, Mar. 1, 1998.
Tolvanen M. Et al., "In Vitro Attachment of Mono-And Oligosaccharides To Surface Glycoconjugates of Intact Cells", The Journal of Biological Chemistry, vol. 261, No. 20, pp. 9546-9551, Jul. 20, 1986.
Kim S.A. et al., "The Use of Palmitate-Conjugated Protein a For Coating Cells With Artificial Receptors Which Facilitate Intercellular Interactions" Journal of Immunological Methods, vol. 158, pp. 57-65, 1993.
Medof M.E. et al., "Cell Surface Engineering With GPI-Anchored Proteins" Faseb Journal, vol. 10, No. 4, pp. 574-586, Apr. 1996.

* cited by examiner

*Primary Examiner*—Gailene R Gabel
(74) *Attorney, Agent, or Firm*—Nixon & Vanderhye

(57) ABSTRACT

The invention provides for a process for preparing a sensitivity control for blood group determination including dissolving an amount of an antigen in water to give an antigen solution of known concentration, contacting the antigen solution with cells to allow insertion of antigen molecules into the cell membranes of the cells to give transformed cells or contacting the antigen solution with cells that have been modified by the insertion of a linker molecule into the membranes of the cells to allow attachment of antigen molecules to the linker molecules to give transformed cells, washing the transformed cells to give a transformed cell solution, and determining the concentration of the transformed cell solution to enable the solution to be used as a sensitivity control for blood group determination.

8 Claims, 5 Drawing Sheets

SENSITIVITY CONTROLS FOR BLOOD SEROLOGY PREPARED FROM MODIFIED CELLS

This invention relates to the use of artificially modified cells which express blood group (or blood group related) antigens to give cells useful in immunohaematology/haematology/immunology/serology assays as sensitivity controls. In particular, the invention relates to sensitivity controls for use in transfusion medicine which have been prepared from cells into which A and/or B antigens have been inserted.

BACKGROUND

A critical function of blood centres is the testing of blood to accurately determine the blood group type of the individual from whom the blood (or other product) was obtained. Knowledge of the blood group type is essential for a variety of therapies including blood transfusion, organ transplantation, and the treatment of haemolytic diseases of the newborn. In particular, an individual's blood group type must be determined prior to being given a blood transfusion. A mismatch of blood group types can have disastrous consequences potentially leading to the death of the transfused individual.

The ABO blood group system represents the most important of the antigens on human red blood cells (RBCs) for blood transfusion serology. Humans belong to one of four major groups: A, B, AB, and O. The RBCs of each group respectively carry the A antigen, the B antigen, both A and B antigens, or neither. Natural antibodies are present in the blood against the blood group antigen which is absent from the RBCs. Thus, individuals of group A have anti-B, those of group B have anti-A, those of group O have anti-A and anti-B, and those of group AB have neither. Before blood transfusion the blood must be cross-matched (either by testing the donor blood against the serum of the recipient or by electronically matching the blood against records) to ensure that RBCs of one group are not given to an individual possessing antibodies against them.

RBCs are tested against reagents containing known antibodies (known as forward grouping) and serum is tested against RBCs possessing known antigens (known as reverse grouping).

Monoclonal antibodies (MAbs) have been used as blood typing reagents since the 1980's. When compared with traditional polyclonal antisera, monoclonal reagents offer increased specificity, consistent reactivity, and, in most cases, increased potency.

Routine quality control of blood group systems (for example, gel cards) and reagents is essential in any blood bank laboratory. Reagents and blood grouping systems may suffer reductions in specificity or potency during shipping, storage, or as a result of contamination during storage and use.

Monoclonal reagents are required to identify all natural variations of ABO blood groups including subgroups of A and B. To ensure correct identification, monoclonal blood grouping reagents and blood grouping systems in blood bank laboratories are tested against RBC reagent controls. For this purpose, RBCs with a weak antigen expression are preferred as the control reagent. This is because such RBCs can provide a better indication of an antiserum's potency for the identification of weak phenotypes.

There exist in nature various forms of weak or poorly expressing ABO subgroups. The A/B antigen concentrations within each of the cell phenotypes are variable and generally unknown unless extensive analysis is performed.

Using weak phenotyping RBCs as control reagents is difficult in practice, due to the very low frequency of subgroup phenotype individuals. For example, the Ax phenotype is estimated as 0.003% of group A and other subgroups have even lower frequency. Artificial weak phenotype RBCs may therefore be useful for this purpose.

Group O RBCs transformed into artificial group A RBCs or group B RBCs or group AB RBCs appear to resemble weak phenotypes serologically. Expression of these antigens can be controlled by changing the insertion conditions, such as the concentration of inserted antigen, and/or the ratio of RBC to antigen for insertion or amount of synthetic antigen added etc. The inserted antigens can be stable in the RBC membrane in certain conditions for at least six weeks, and possibly longer.

Currently, serological sensitivity of monoclonal antibodies (antisera) used for the detection of cells that poorly express carbohydrate antigens can be determined in one of several ways:

1. Testing against natural weak subgroups. This involves finding a rare subgroup, preparing cells of this subgroup ready for use, and then using them as controls.
2. Testing against normal cells. This involves testing common cells and does not give any indication of sensitivity.
3. Diluting antisera to determine potency. This involves diluting antibodies and testing against normal antigens. This is the most common practice in the absence of true controls.

Natural cells, due to their frequency, are very difficult to obtain and maintain supply. In addition, they vary between individuals. Constant supply would be difficult, if not impractical. Further, different populations have different frequencies of weak subgroups.

Normal cells express high levels of antigen, for example in the region of >500,000 copies per red cell. When testing these cells, the reagents are typically diluted to show that at low dilution they can still react with RBCs and give a serologically positive result. This dilution sensitivity method is time consuming. The results are then extrapolated to determine the detection level of antigen at normal dilution. This flawed methodology is unfortunately the practice in most places. Detection of reagent deterioration would only be possible if regular time consuming dilution studies were undertaken or weak subgroups were tested.

Additional problems can occur with the dilution of antisera. Monoclonal reagents are often biclonal and formulated to give specific performance characteristics. It is well known that some clones are better than others at detecting ABO subgroups. As a consequence, reagents are often formulated as blends. Dilution of such reagents negates their intrinsic performance features and thus will not reflect the true performance of the reagents Furthermore, many monoclonal reagents now come formulated for and pre-loaded into test card systems (i.e. gel cards) and thus cannot be tested by dilution methods.

Many laboratories do not presently routinely carry out sensitivity controlling of their ABO blood typing reagents. Instead they rely upon the manufacturer and the historical performance of the reagents. Alternatively, laboratories may only batch test on a weekly or even monthly basis in the manner described for 3 above. Furthermore, many rely on the literature outcomes of accidental transfusion of a weak subgroup to an incompatible recipient, which indicates that these events are usually non-fatal. Previously, a cross-match (the testing of the donor's blood against the recipient's serum) would detect an incompatibility between a weak subgroup mistyped and for transfusion to an incompatible recipient. However, these days cross-matching is not performed in many centres and instead correct blood typing of both the donor and recipient is relied upon. It is therefore now more important that blood is accurately typed. The problem of not carrying out any testing is that the blood typing reagents may have deteriorated and a clinically significant subgroup may be incorrectly blood typed in the absence of cross-matching. Such blood may cause a mild to severe transfusion reaction.

There is therefore a clear need for sensitivity control reagents which have a known predetermined amount of antigen expression and are therefore capable of being used to calibrate testing reagents or testing systems to give accurate and standardised determinations of blood group types.

It is an object of this invention to provide a sensitivity control reagent for blood group determinations, or to at least provide a useful alternative.

STATEMENTS OF INVENTION

In one aspect of the invention there is provided a process for preparing a sensitivity control for blood group determination including:
  contacting a blood group-related glycolipid solution of known concentration with a suspension of cells for a time and at a temperature sufficient to allow insertion of the blood group-related glycolipid molecules into the cell membranes of the cells to give transformed cells; or
  contacting a biotinylated blood group-related carbohydrate solution of known concentration with a suspension of cells that have been modified by the insertion of a linker molecule into the membranes of the cells for a time and at a temperature sufficient to allow attachment of biotinylated blood group-related carbohydrate molecules to the linker molecules to give transformed cells; and
  washing the transformed cells with a washing solution and suspending the washed transformed cells in water optionally containing one or more dissolved salts to give a transformed cell solution; and
  determining the concentration of the transformed cell solution to enable the solution to be used as a sensitivity control for blood group determination.

In one embodiment of the invention the cells of the suspension are not modified and the transformed cells comprise blood group-related glycolipid molecules inserted directly into the cell membranes.

In an alternative embodiment of the invention the cells of the suspension are modified by the insertion of a linker molecule and the transformed cells comprise blood group-related carbohydrate molecules attached to the cell membranes via the linker molecules.

The cells used may be any cell type including animal cells, plant cells, bacterial cells, or cells or vesicles having an artificial cell membrane. However, it is preferred that the cells used are animal cells. It is further preferred that the animal cells are human red blood cells.

It is preferred that the linker molecule includes a lipid tail and a bridge that joins the lipid tail to the antigen.

The linker molecule preferably contains a biotinylated glycolipid. One example of the bridge is a biotin-avidin bridge.

Preferably the blood group-related glycolipid is an A, B, H, Lewis, or Gal(alpha) glycosphingolipid. It is also preferred that the biotinylated blood group-related carbohydrate is A, B, H, Lewis, or Gal(alpha).

In a second aspect of the invention there is provided a transformed cell obtained by the process of the first aspect of this invention.

In another aspect of the invention there is provided a process for the determination of the sensitivity of a blood group testing reagent or testing system including:
  contacting an amount of a sensitivity control obtained by the process of the first aspect of this invention with the blood group testing reagent or testing system to allow antigen-antibody reactivity between the transformed cells and antibodies or lectins contained in the testing reagent or testing system;
  assessing the level of antigen-antibody reactivity; and
  determining the sensitivity of the blood group testing reagent or testing system.

The assessment of the level of antigen-antibody reactivity may be by assessing direct agglutination or by induced agglutination. Induced agglutination includes potentiation or the use of antiglobulin molecules or by using enzymes.

Preferably the assessment is by the use of enzyme labels, radioactive labels, or fluorescence labels.

In a further aspect of the invention there is provided the use of a sensitivity control obtained by the process of the first aspect of the invention for measuring the effectiveness of one or more reagents or testing systems used in blood group determinations.

In another aspect of the invention there is provided a kit containing components suitable for carrying out a blood group determination where the kit includes a sensitivity control obtained by the process of the first aspect of this invention.

DETAILED DESCRIPTION

Figure 1:
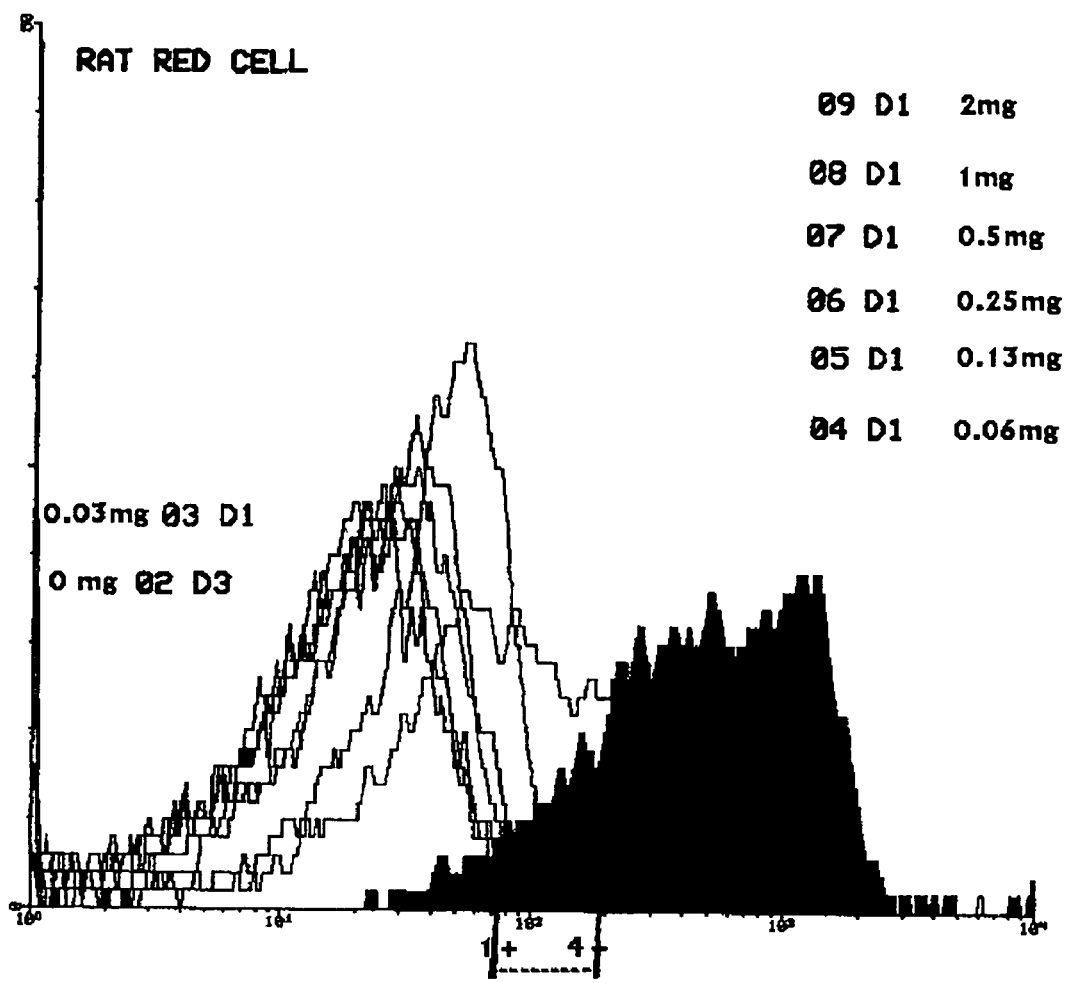
FIG. 1 shows the flow cytometry results of varying the amount of glycolipid $Le^b$ on in vivo transformation of rat peripheral blood cells using anti-$Le^b$ as the primary antibody

Although much of the following description refers to glycosphingolipid antigens, it is to be appreciated that other antigens, including other glycolipids and synthetic antigens are also encompassed by the invention. It is also to be appreciated that the term "antigen" includes modified antigens such as antigens having an attached molecule enabling binding to a linker molecule. For example, in the case of a linker molecule ending in an avidin, the antigen will be a biotinylated antigen.

Linker molecules may be a lipid which is inserted into the membrane of a cell capable of linking an antigen to the membrane of the cell. A carbohydrate part will typically be joined to the lipid by a bridge, such as a biotin-avidin bridge. Other bridges may, however, be used such as any bridge based on chelation binding.

For the avoidance of doubt, any reference in this specification to a solution of cells is intended to include a suspension of cells.

Glycolipids as blood group antigens can be taken up by RBCs from plasma. This knowledge came partly from studies of the Lewis system. Plasma lipids exchange with lipids in the RBC membrane and the composition of phospholipids and fatty acids in RBC membranes resembles that in plasma. Consequently, plasma glycosphingolipids bearing Lewis or ABH structures become incorporated into the RBC membrane.

Insertion technologies are based on established principles that glycolipid antigens can insert into the red cell membrane without damaging the cell. The amount of antigen inserted/expressed can be controlled thereby creating cells with specific performance characteristics. These cells can either resemble natural weak subgroups or unnatural (not naturally occurring) blood group expressing cells.

The amount of antigen expressed on the cells can be set according to the requirements of the users. Different levels of expression are possible, for example 5%, 10%, 20%, or 1000 copies, 5000 copies, etc per red cell. One control may be set at the clinical threshold at which failure to detect an antigen may result in a clinically significant transfusion reaction. Other controls can be set at levels that will ensure confidence in the detection of weak subgroups. These controls can validate the performance of ABO blood grouping tests by making the sensitivity levels measurable. This can ensure the provision of safer ABO grouped blood.

The sensitivity control of the invention is useful for determining the sensitivity of blood group testing reagents and/or testing systems, including gel cards.

Weak subgroup sensitivity controls for use in transfusion medicine are made from group O cells into which specific amounts of A and/or B antigens are inserted to give specific reaction scores in antigen detection assays. The assays may include tile, tube, gel card, and microplate methods, and any manual or automated platform which uses agglutination, or any other method of antigen detection (for example, enzyme linked immunoassay, flow cytometry etc).

Although it is preferred to use human RBCs for the invention, the RBCs of other animals can be used. In addition, while the following description refers principally to RBCs, it is to be appreciated that other cells such as platelets, white cells, plant cells, cell culture cells, bacterial cells and artificial cell membranes may be used.

Red blood cells expressing inserted antigens can be created either in vitro or in vivo using human or other animal cells. Creating cells in vivo requires injecting specific amounts of antigen into the circulation system of a human or other animal and then obtaining the blood either immediately or over timed periods. The latter produces decreasing amounts of expressed antigen (effectively a natural titre). This method can be used to create cells expressing some antigens but not others. For example, animal RBCs can be used to create ABO typing RBCs which are negative for the human Kell, Duffy, Rhesus, or Kidd antigens.

Agglutination is one measure for antigen detection. Agglutination is the clumping of red cells caused by antibody or lectin crosslinking the antigens on different cells. Agglutination can be visualised manually (by eye) or in automated techniques by blood group analysers. Manual agglutination reactions can be scored according to the following scheme:

| Agglutination Score | Observations |
| --- | --- |
| − | no clumps at all |
| (+) | indeterminant |
| vw | very weak reactivity—visible only with optical aid |
| w or +w | weak—very very small clumps |
| + | very small clumps |

-continued

| Agglutination Score | Observations |
| --- | --- |
| ++ | several small clumps |
| +++ | one large clump surrounded by small clumps |
| ++++ | one single large clump |

The higher the concentration of group A or group B antigen solution used for insertion, the greater the amount of antigen inserted into group O RBCs. This is seen by the stronger agglutination of the transformed RBCs with anti-A or anti-B reagents. Lower concentrations of group A or group B antigen solutions lead to the insertion of less A or B antigens into group O RBCs, resulting in weaker agglutination with anti-A or anti-B reagents. The amount of inserted antigens is proportional to the concentration of the glycolipid insertion solution and/or temperature and/or time of contact.

RBCs can be transformed with short or long chain glycolipids. However, there appears to be no significant difference between these two types of transformed RBCs in general blood serology when testing against cell typing reagents. Similar agglutination is observed with both types when tested against a specific antiserum. However, RBCs can be transformed with specific components of the ABO system. For example RBCs expressing components of the A antigens (such as $ALe^b$ or A type 3) can be created. Such cells would be important for determining the specificity of certain antibodies and in the screening of monoclonal antibody panels.

The effect of the ratio of RBC concentration to glycolipid concentration is that a ratio of between 1:1 and 3:1 leads to efficient transformation of group O RBCs and strong agglutination scores with anti-A or anti-B. A ratio of 4:1 or greater leads to less insertion of antigens. In certain conditions, 3:1 is the most economical ratio to give a strong serological score. However, a higher ratio of RBCs may be used if a weak phenotype is desired.

Concentrated glycolipid solutions can effectively insert antigens into RBCs within two hours. Longer incubation times result in better insertion, although after extended times (32 hours) the serology deteriorates (see Example 5). This deterioration is considered to be due to the deterioration of the RBCs after prolonged incubation at 37° C., rather than the loss of antigen.

The time taken for insertion of antigen molecules into the membranes of the cells depends on the relative concentrations of the antigen solution and the cell solution and temperature. However, it is preferred that for an antigen solution with a concentration of approximately 10 mg/ml and a ratio of packed red blood cells of 3:1 at 25° C., the insertion time is approximately 4 hours.

Changes in the insertion conditions can allow the controlling of antigen expression on RBCs. If weak A or weak B cells are desired, then low glycolipid concentration or high RBC:glycolipid ratios can be used for insertion. If strongly agglutinating phenotypes are needed, high concentrations of glycolipid solution or lower RBC:glycolipid ratios can give the strongest serology. By manipulating glycolipid concentrations, RBCs can be "created" which express more than 20 times the amount of antigen normally found in the RBC membrane.

The primary advantage of the invention is that the amount of antigen expression can be controlled to meet specific sensitivity requirement. For example, one cell could contain the number of antigens which correlates with a clinical significance level. Therefore, if this cell produces a positive serology result then the user can be assured they will not miss any clinically significant subtypes.

Another cell could be set at specific antigen thresholds, for example one for each of the different subtypes thereby allowing for known levels of sensitivity. Such cells could also be used to calibrate highly sensitive machines or could even be used in flow cytometry analysis for antigen quantitation curves.

The methodology allows cells to be standardised and be consistent worldwide. This would allow comparisons of the performance of different laboratories and different methodologies. Inclusion of the cells in Transfusion Serology Quality Assurance Programmes could set the 'standard' for the quality control of ABO blood group testing.

There is a compelling need in the industry for sensitivity controls. The importance of this is magnified because there is general movement in pathology towards laboratories staffed by multi-skilled technicians who do not have extensive blood transfusion experience.

The sensitivity control of this invention preferably is a set of a group A (weak) phenotype and a group B (weak) phenotype. It is further preferred that one would also be Rh DCce (R1r) and the other Rh ce(rr). This would ensure that both the ABO and RhD grouping reagents could be quality controlled by the same set of cells. Additionally, another set with a range of weak AB antigens may be useful for more specialised laboratories. Alternatively, animal cells lacking specific human antigens could be used. For example, some animal cells would be the equivalent of Rh null (i.e. lacking Rh antigens).

Some laboratories perform ABO and RhD quality control effectively, but others do not. Some laboratories manufacture in-house ABO and RhD quality control cells (A2B R1r, O rr). However, there is a degree of variation in these products because of blood donor phenotype heterogeneity. The sensitivity controls of this invention do not suffer this disadvantage because the weakened antigenic expression is precise, there is a lack of variability, and they are readily available.

A further advantage of the invention is that the insertion fluid containing the antigen may be dried and stored without deterioration for long periods of time. Reconstitution of the transforming solution and its addition to cells could allow for the creation of small volumes of specialised cells as required, for example, acquired B. Such products do not currently exist.

EXAMPLES

The following examples are intended simply to illustrate the invention. The invention is not to be considered as limited by any of the examples.

Example 1

Glycolipid insertion solutions were prepared according to the following method:
Dried glycolipid was dissolved in chloroform:methanol (2:1) to a concentration of 20 mg/ml.
200 µl of the glycolipid solution was aliquoted into a glass tube and dried under nitrogen gas.
300 µl methanol:water (1:1) was added to dissolve the dried glycolipid. The tube was warmed to 37° C. in water bath to help dissolution.
The tube was marked at the 100 µl level, and the glycolipid solution was dried at 60° C. with nitrogen gas to below the mark. This step evaporates most of the methanol in the solution and leaves the glycolipid dissolved in water.
10 µl of 10× phosphate buffered saline (PBS) was added to the tube in order to adjust the salt concentration.
Deionised water was added to the 100 µl level.

Example 2

Glycolipids were inserted into RBCs according to the following method:
5 µl of 40 mg/ml of glycolipid insertion solution was added to a glass culture tube.
15 µl of Celpresol and 40 µl of group O packed RBCs were added.
The tube was incubated at 37° C. for two hours with constant shaking.
The transformed RBCs were washed 6× with 0.9% saline before being suspended in Celpresol at a concentration of 5%.
Celpresol is an RBC preservative solution (obtained from CSL Biosciences, Adelaide, Australia). However, saline or other isotonic solutions, or cell storage solutions (e.g. Cell-Stab) may be used.

Example 3

The following example is one method for testing an antiserum using a control of the invention:
1. Transformed RBCs were washed 3× with 0.9% saline. Celpresol was added to the tubes to make an RBC suspension of 5% concentration.
2. The RBC suspension (25 µL) was added to a small glass tube. Antiserum (25 µL) was then added.
3. The RBC suspension and the antiserum were mixed well and spun in an immunofuge for 15 seconds.
4. The amount of agglutination was read and scored.

Example 4

Examples of serological phenotyping antibodies available which can be tested using the controls of this invention are shown below. This list of examples is not exhaustive and other antibodies may be applicable to this invention. Some of these reagents tested were expired and were used for demonstrative purposes only.

| Name | Manufacturer |
| --- | --- |
| Anti-A: | |
| Bio-Clone (blend) | Ortho Diagnostic, USA |
| Biolab (Human) 1 | Biological Laboratories, NZ |
| Biolab (Human) 2 | Biological Laboratories, NZ |
| Biolab | Biological Laboratories, NZ |
| Epiclone 1 | CSL, AUS |
| Epiclone 2 | CSL, AUS |
| Epiclone 3 | CSL, AUS |
| Epiclone 4 | CSL, AUS |
| Gamma-clone 1 | Gamma Biologicals, USA |
| Gamma-clone 2 | Gamma Biologicals, USA |
| Immucor | Immucor, USA |
| Lorne | Lorne Laboratories, UK |
| MonoClone | Organon Teknika B.V. NL |
| Novaclone | Dominion Biologicals, Canada |
| Ortho | OCD, USA |
| Seraclone 1 | Biotest AG, Dreieich |
| Seraclone 2 | Biotest Diagnostic, Dreieich |
| *CSL | CSL, AUS |
| *XXX$_1$ | Confidential |
| *XXX$_2$ | Confidential |
| Anti-B: | |
| Biolab (Human) | Biological Laboratory, NZ |
| Biolab | Biological Laboratory, NZ |

-continued

| Name | Manufacturer |
|---|---|
| BioClone (blend) | Ortho Diagnostic, USA |
| Epiclone 1 | CSL, AUS |
| Epiclone 2 | CSL, AUS |
| Gamma-clone | Gamma Biologicals, USA |
| Immucor | Immucor, USA |
| Lorne | Lorne Laboratories, UK |
| Monoclone | Organon Teknika B.V. NL |
| Novaclone | Dominion Biologicals, Canada |
| Seraclone | Biotest AG, Dreieich |
| *CSL | CSL, AUS |
| *XXX$_3$ | Confidential |
| *XXX$_4$ | Confidential |
| *XXX$_5$ | Confidential |
| Anti-AB: | |
| Biolab (Human) | Biological laboratories, NZ |
| Biolab | Biological laboratories, NZ |
| Gamma (blend) | Gamma Biologicals, USA |
| Immucor | Immucor, USA |
| Seraclone 1 | Biotest Diagnostics, Dreieich |
| Seraclone 2 | Biotest Diagnostics, Dreieich |

*Developmental reagents

Example 5

The incubation time of glycolipid insertion was investigated by adding 180 μl of packed group O RBCs to 60 μl of 9.6, 4.8, 2.4, 1.2 and 0.6 mg/ml long chain A or short chain B glycolipid solutions, respectively. A 25 μl aliquot was removed after incubation with glycolipids for 1, 2, 4, 8, 24, 48 and 72 hours. Serology tests were performed on the cells. The results are summarised in Table 1 and Table 2.

TABLE 1

Study on insertion incubation time: group O RBCs transformed with neutral A glycolipids and tested against Bioclone anti-A

| A glycolipid concentration of transformation medium (mg/ml) | Incubation Time (hours) | | | | | | | |
|---|---|---|---|---|---|---|---|---|
| | 1 | 2 | 4 | 8 | 24 | 32 | 48 | 72 |
| 9.6 | +++ | ++++ | ++++ | ++++ | ++++ | ++++ | ++++ | ++++ |
| 4.8 | +++ | +++ | ++++ | ++++ | ++++ | ++++ | +++ | +++ |
| 2.4 | ++ | +++ | +++ | +++ | +++ | ++++ | +++ | +++ |
| 1.2 | − | + | + | + | ++ | +++ | ++ | ++ |
| 0.6 | − | − | + | + | + | ++ | ++ | ++ |

TABLE 2

Study on insertion incubation time: group O RBCs transformed with neutral B glycolipids and tested against XXX$_5$ anti-B.

| B glycolipid concentration of transformation medium (mg/ml) | Incubation Time (hours) | | | | | | | |
|---|---|---|---|---|---|---|---|---|
| | 1 | 2 | 4 | 8 | 24 | 32 | 48 | 72 |
| 9.6 | + | ++ | +++ | +++ | +++ | ++++ | +++ | +++ |
| 4.8 | + | ++ | +++ | +++ | +++ | ++++ | +++ | +++ |
| 2.4 | − | + | + | + | ++ | +++ | +++ | +++ |
| 1.2 | − | − | − | − | − | − | ++ | ++ |
| 0.6 | − | − | − | − | − | − | − | − |

Example 6

Different volumes of packed group O RBCs were transformed with one volume of 9.6 mg/ml long chain A or B glycolipid solution, respectively. The results are summarised in Table 3. A 3:1 ratio of RBCs to plasma (glycolipid insertion solution) appeared as efficient as a 1:1 ratio for insertion. When the amount of RBCs was increased to 4:1, 5:1, and 6:1, then the amount of insertion per RBC decreased.

TABLE 3

Study of ratio of RBC to glycolipid insertion fluid (plasma). Different volumes of group O RBCs transformed with group A or B glycolipids and tested against anti-A or anti-B reagents.

| RBC:Glycolipid | Inserted A reacted against anti-A | Inserted B reacted against anti-B |
|---|---|---|
| 1:1 | ++++ | ++++ |
| 2:1 | ++++ | ++++ |
| 3:1 | ++++ | ++++ |
| 4:1 | ++ | +++ |
| 5:1 | ++ | ++ |
| 6:1 | ++ | ++ |

Anti-A: Bioclone;
Anti-B: CSL.

Example 7

A wide variety of anti-A, anti-B and anti-AB reagents were tested for their potency against RBCs transformed with neutral A and B glycolipids using the method of this invention. The RBCs were tested on the day of insertion.

Group O RBCs inserted with neutral A glycolipids were tested against anti-A reagents from different manufacturers. The results are shown in Table 4.

TABLE 4

Group A glycolipid transformed O RBCs tested against different anti-A reagents (sorted by scoring patterns).

| Manufacturer | A glycolipid concentration of transformation media (mg/ml) | | | | | | | |
|---|---|---|---|---|---|---|---|---|
| | 9.6 | 7.2 | 4.8 | 3.6 | 2.4 | 1.9 | 1.2 | 0.6 |
| *XXX$_2$ | ++++ | ++++ | ++++ | +++ | +++ | ++ | ++ | ++ |
| Bio-Clone | ++++ | +++ | +++ | +++ | ++ | ++ | + | − |
| Seraclone | ++++ | +++ | +++ | ++ | + | + | w | − |
| *CSL | ++++ | +++ | +++ | ++ | ++ | + | − | − |
| Novaclone | +++ | ++ | ++ | + | − | − | − | − |
| *XXX$_1$ | +++ | ++ | ++ | + | + | − | − | − |
| Ortho | ++ | ++ | + | w | − | − | − | − |
| Epiclone 1 | ++ | + | + | − | − | − | − | − |
| Epiclone 2 | + | + | − | − | − | − | − | − |
| Lorne | + | w | w | − | − | − | − | − |
| Gamma-clone 1 | + | − | − | − | − | − | − | − |
| Seraclone 1 | + | − | − | − | − | − | − | − |
| Immucor | + | − | − | − | − | − | − | − |
| Epiclone 1 | + | − | − | − | − | − | − | − |
| Biolab (human) 1 | + | − | − | − | − | − | − | − |
| Monoclone | w | − | − | − | − | − | − | − |
| Biolab | − | − | − | − | − | − | − | − |
| Biolab (human) 2 | − | − | − | − | − | − | − | − |

*Developmental reagents.

Reagents from different manufacturers (some well beyond their expiry dates) gave enormous differences in agglutination scores. As seen from Table 4 (sorted by scoring patterns), when the group A insertion glycolipid concentration is 9.6 mg/ml, several anti-A reagents gave 4+ or 3+ agglutination scores with transformed RBC, while others gave only 1+ or negative reactions. At a 0.6 mg/ml concentration, only the $XXX_2$ developmental reagent could detect inserted antigens.

Group O RBCs transformed with neutral A glycolipids were also tested against anti-AB reagents from different manufacturers. The results are shown in Table 5. Anti-AB reagents also gave different agglutination scores with transformed RBCs.

TABLE 5

Group A glycolipid transformed O RBCs tested against different anti-AB reagents.

| Manufacturer | A glycolipid concentration of transformation media (mg/ml) | | | | | | | |
|---|---|---|---|---|---|---|---|---|
| | 9.6 | 7.2 | 4.8 | 3.6 | 2.4 | 1.9 | 1.2 | 0.6 |
| Immucor | +++ | ++ | ++ | + | + | – | – | – |
| Gamma-clone | +++ | ++ | ++ | + | + | – | – | – |
| Seraclone | ++ | ++ | ++ | w | – | – | – | – |
| Biolab | ++ | ++ | ++ | w | – | – | – | – |
| Biolab (Human) | ++ | + | + | – | – | – | – | – |
| Seraclone | ++ | + | + | – | – | – | – | – |

Group B glycolipid transformed O RBCs were also tested against anti-B reagents from different manufacturers. The results are shown in Table 6.

TABLE 6

Group B glycolipid transformed O RBCs tested against different anti-B reagents (sorted by scoring pattern).

| Manufacturer | B glycolipid concentration of transformation media(mg/ml) | | | | | | | |
|---|---|---|---|---|---|---|---|---|
| | 9.6 | 7.2 | 4.8 | 3.6 | 2.4 | 1.9 | 1.2 | 0.6 |
| *CSL | +++ | +++ | +++ | +++ | ++ | + | + | – |
| *$XXX_5$ | ++ | ++ | ++ | + | + | – | – | – |
| *$XXX_3$ | ++ | ++ | ++ | + | – | – | – | – |
| Bioclone | + | + | w | – | – | – | – | – |
| Biolab | w | – | – | – | – | – | – | – |
| Biolab (human) | – | – | – | – | – | – | – | – |
| Epiclone | – | – | – | – | – | – | – | – |
| Epiclone | – | – | – | – | – | – | – | – |
| *$XXX_4$ | – | – | – | – | – | – | – | – |
| Novaclone | – | – | – | – | – | – | – | – |
| Monoclone | – | – | – | – | – | – | – | – |
| Gammaclone | – | – | – | – | – | – | – | – |
| Seraclone | – | – | – | – | – | – | – | – |
| Immucor | – | – | – | – | – | – | – | – |
| Lorne | – | – | – | – | – | – | – | – |

*Developmental reagents

Only very few anti-B reagents could detect the inserted group B antigens. Among those reagents which did, only Bioclone is a commercial anti-B reagent. Others are developmental reagents.

Group B glycolipid transformed group O RBCs were also tested against anti-AB from different manufacturers. The results are shown in Table 7.

TABLE 7

Group B glycolipid transformed O RBCs tested against different anti-AB reagents.

| Manufacturer | B glycolipid concentration of transformation media (mg/ml) | | | | | | | |
|---|---|---|---|---|---|---|---|---|
| | 9.6 | 7.2 | 4.8 | 3.6 | 2.4 | 1.9 | 1.2 | 0.6 |
| Biolab (human) | +++ | ++ | ++ | + | + | – | – | – |
| Biolab | + | w | w | – | – | – | – | – |
| Immucor | – | – | – | – | – | – | – | – |
| Seraclone | – | – | – | – | – | – | – | – |
| Seraclone | – | – | – | – | – | – | – | – |
| Gamma-clone | – | – | – | – | – | – | – | – |

Only Biolab anti-AB could detect inserted group B antigens. This is a human polyclonal anti-A+B reagent (which is no longer commercially available).

Example 8

$Le^b$ glycolipid can insert into RBCs when the $Le^b$ glycolipid is suspended in Le(b–) plasma and mixed with RBCs of the same type in different ratios and incubated for two hours at 37° C. The results are shown in Table 8.

TABLE 8

Uptake of $Le^b$ glycolipid onto Le(b–) cells.

| RBC | $Le^b$: RBC (v/v) | Reactions with antisera Time 0 | | Reactions with antisera 1 Week | |
|---|---|---|---|---|---|
| | | –$Le^b$ | –$Le^a$ | –$Le^b$ | –$Le^a$ |
| Le(a+b–) before insertion | | – | ++ | – | ++ |
| After insertion | 1:2 | ++ | ++ | +++ | ++ |
| | 1:3 | ++ | ++ | +++ | ++ |
| | 1:5 | ++++ | ++ | +++ | ++ |
| | 1:7 | ++ | ++ | +++ | ++ |
| | 1:10 | ++ | ++ | +++ | ++ |
| Le(a–b–) before insertion | | – | – | – | – |
| After insertion | 1:2 | + | – | ++ | – |
| | 1:3 | ++ | – | ++ | – |
| | 1:5 | +++ | – | ++++ | – |
| | 1:7 | ++ | – | ++ | – |
| | 1:10 | ++ | – | ++ | – |

Example 9

This example describes the procedure used for flow cytometry analysis.

Flow cytometric analyses were performed on a Facsort instrument (Becton Dickinson, San Jose, Calif.) operating with Lysis II software. Washed rat red cells were fixed by adding one part of red cells to 20 parts of 10% formalin and incubating overnight at room temperature. The fixed cells were washed 4 times in PBS and diluted in 0.5% BSA in buffer 1 (phosphate buffered 50 mM NaCl, pH 8.0) to a final concentration of $5 \times 10^6$ cells/ml before incubation with the Lewis antibodies. Fluorescent labelling conditions used were based on the work of Murai et al. (Clinica Chimica Acta, 1994, 226, 21-28). For analysis, 100 μl of fixed red cell suspension were incubated at 4° C. for 1 h with 100 μl of anti-Le$^b$ (Gamma 25-1, Gamma Biologicals Inc., Tx, diluted 1:2 in buffer 1), washed twice in 1 ml of buffer 1 and incubated at 4° C. for 1 h with 100 μl of biotinylated anti-mouse IgM (E0465, Dako A/S, Denmark; diluted in buffer 2, 1:400 in 0.5% BSA in phosphate buffered 200 mM NaCl, pH 8.0). Labelled cells were then washed twice in 1 ml of buffer 2 and incubated at 4° C. for 10 minutes with 100 μl of RPE-Streptavidin (R0438 Dako A/S, diluted 1:15 in buffer 3, phosphate buffered 200 mM NaCl, pH 7.0), washed once in and then suspended in 500 μl of buffer 3. Flow cytometric analysis was within 1 hour, with 5000 cells being counted for each sample.

Example 10

The in-vivo transformation of rat peripheral blood cells was accomplished using the following method.

Large (250-300 g), inbred, all male Lewis rats were used. These rats, despite their name, do not to express Le$^a$ or Le$^b$ glycolipids.

Glycolipids were emulsified into Emulsan®, a parenteral lipid infusion fluid which contains 20% soy oil fraction, 1.2% lecithin/egg white, and 22% glycerol, w/v. Serial dilutions with glycolipid concentrations ranging from 0.03 to 2.0 mg/150 μl were prepared from a stock solution (13.3 μg/μl) of glycolipid in Emulsan®. After anaesthesia (8% chloralhydrate at a dose of 3.3 ml/kg) the jugular vein of rats was surgically exposed and 150 μl of a glycolipid/Emulsan® dilution was infused. The operation site was then sutured.

At 24 hours and thereafter approximately 50 μl of red cells were obtained by warming the rats under heat lamps, applying a tourniquet to the tail, and making a small puncture of a tail vein with a microlance and obtaining blood. Red cells were obtained from the whole blood by centrifugation and washing three times. Other cells (e.g. platelets, white cells) can be obtained by appropriate isolation techniques. Serology and flow cytometry analyses were undertaken and are described in Examples A to C below.

Example A

Serology with anti-Le$^b$ analysis of in vivo transformation of rat red cells. Rats were injected intravenously with different doses of Le$^b$-6 glycolipids. Blood samples were taken on the days indicated in Table 9. Serological direct agglutination with anti-Le$^b$ was graded from negative (−) to very strongly positive (++++).

Example B

In vivo glycolipid anti-Le$^b$ flow cytometry relationship. Different rats were injected with different doses of Le$^b$ glycolipids and bled after one day. The results are shown in FIG. 1. The zone of positive serology is shown 1+- - - 4+. The highest amount of glycolipid used for transformation (2 mg) produced the black filled curve. Unfilled curves decreasing to the left of the 2 mg curve represent the results obtained from decreasing amounts of glycolipid. The doses of glycolipid used were 2 mg, 1 mg, 0.5 mg, 0.25 mg, 0.13 mg, 0.06 mg, 0.03 mg and 0 mg.

Example C

Figure 2:
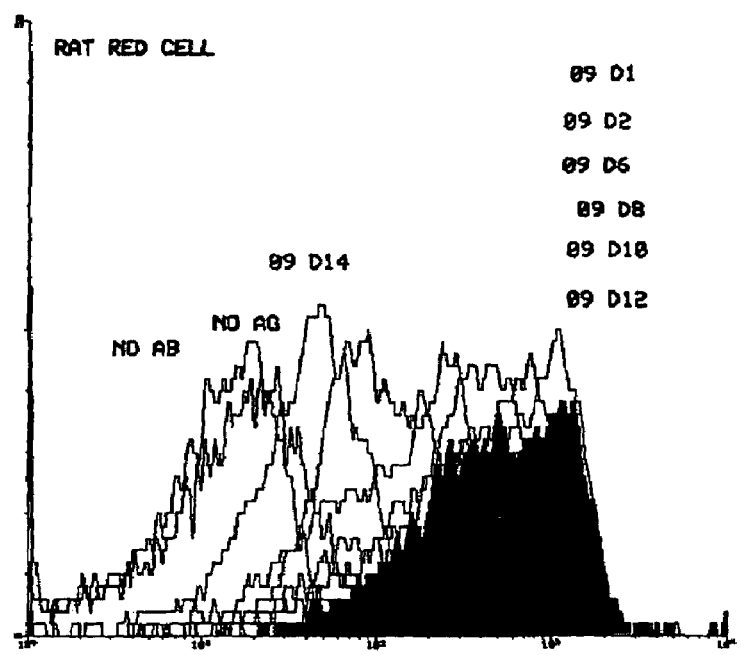
FIG. 2 shows the flow cytometry results of varying the time between 1 to 12 days on in vivo transformation of rat peripheral blood cells using anti-$Le^b$ as the primary antibody.
Figure 3:
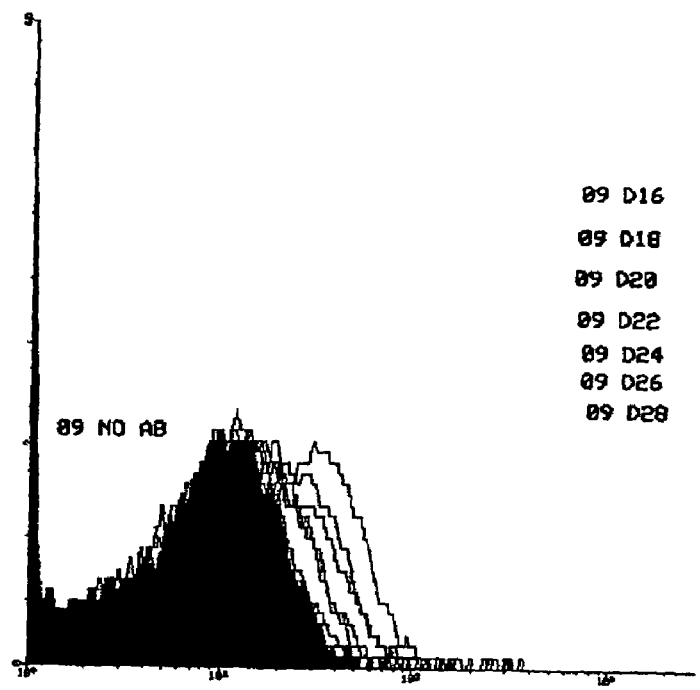
FIG. 3 shows the flow cytometry results of varying the time between 16 to 28 days on in vivo transformation of rat peripheral blood cells using anti-$Le^b$ as the primary antibody.

Flow cytometry anti-Le$^b$ analysis of in vivo transformed rat red cells. A rat was injected with a 2 mg dose of Le$^b$ glycolipids and bled on days 1, 2, 6, 8, 10, 12, 16, 18, 20, 22, 24, 26, 28. The highest level of transformation can be seen in the black filled curve. The results are in sequential order of decreasing antigen expression, ie from right to left being days 1, 2, 6, 8, 10, 12, 14 and negative controls for FIG. 2 and days 16, 18, 20, 22, 24, 26, 28 and the negative control (black filled curve) in FIG. 3

Example 11

Rabbit peripheral blood cells were transformed in vivo using the following method.

Glycolipids were prepared by dissolving 200 mg of total glycolipids (group ALe(a−b+)) from small intestine in 100 μl of warm ethanol. Warm (37° C.) intralipid (Pharmacia) (2 ml) was added followed by brief sonication. Glycolipid was infused into a marginal ear vein (slow infusion). Rabbits were bled pre and post infusion (about 0.2-0.5 ml) and serology tested with anti-Lewis reagents (anti-Le$^b$ Gamma Biological LBM26-1 and sometimes anti-Lea Gamma Biologicals LAM25-1) (see Example D). Testing at later dates also involved retesting earlier samples as controls of stability of stored cells. Cells were stored at 4° C. in red cell preservative solution (Celpresol, CSL Australia).

TABLE 9

| | | Day blood samples were taken (post administration) and red cell anti-Le$^b$ serology conducted | | | | | | | | | | | | | | | | | |
|---|---|---|---|---|---|---|---|---|---|---|---|---|---|---|---|---|---|---|---|
| Rat | mg Le$^b$ | 1 | 2 | 4 | 6 | 8 | 10 | 12 | 14 | 16 | 18 | 20 | 22 | 24 | 26 | 28 | 30 | 32 | 34 | 35 |
| a | 2.0 | ++++ | +++ | ++++ | ++++ | ++++ | ++++ | ++++ | +++ | ++ | ++ | ++ | ++ | ++ | ++ | ++ | + | + | − | − |
| b | 1.0 | +++ | ++++ | +++ | ++++ | +++ | +++ | ++++ | +++ | ++ | ++ | ++ | ++ | ++ | ++ | + | − | − | − | − |
| c | 0.50 | ++ | ++ | ++ | ++ | +++ | +++ | +++ | ++ | + | + | + | + | − | − | − | − | − | − | − |
| d | 0.25 | ++ | ++ | ++ | ++ | ++ | ++ | ++ | + | − | − | − | − | − | − | − | − | − | − | − |
| e | 0.10 | + | + | + | + | − | − | − | − | − | − | − | − | − | − | − | − | − | − | − |
| f | 0.05 | − | − | − | − | − | − | − | − | − | − | − | − | − | − | − | − | − | − | − |
| g | 0.03 | − | − | − | − | − | − | − | − | − | − | − | − | − | − | − | − | − | − | − |
| h | 0 | − | − | − | − | − | − | − | − | − | − | − | − | − | − | − | − | − | − | − |

TABLE 10

Serology—Rabbit MO

| Day sample taken | Day | Date tested | Anti-Le$^b$ | Anti-Le$^a$ |
|---|---|---|---|---|
| Pre (5/10) | −1 | 12/10 | − | − |
| Pre (5/10) | −1 | 8/10 | − | − |
| Infusion 6/10 | 0 | 12/10 | | |
| Post 7/10 | 1 | 8/10 | +++ | − |
| Post 7/10 | 1 | 12/10 | +++ | − |
| Post 9/10 | 3 | 12/10 | +++ | − |
| Post 11/10 | 5 | 12/10 | +++ | − |
| Post 11/10 | 5 | 17/10 | +++ | − |
| Post 11/10 | 5 | 24/10 | +++ | − |
| Post 16/10 | 11 | 17/10 | +++ | − |
| Post 24/10 | 19 | 25/10 | +++ | |

TABLE 11

Serology—Rabbit BK

| Day sample taken | Day | Date tested | Anti-Le$^b$ |
|---|---|---|---|
| Pre (8/8) | | 8/8 | − |
| Infusion 18/10 | 0 | | |
| Post (19/10) | 1 | 20/10 | +++ |
| Post (24/10) | 6 | 25/10 | +++ |
| Post (31/10) | 13 | 3/11 | +++ |

TABLE 12

Serology—Rabbit CO

| Day sample taken | Day | Date tested | Anti-Le$^b$ | Anti-Le$^a$ |
|---|---|---|---|---|
| Pre (5/10) | −13 | | − | − |
| Pre (11/10) | −7 | | − | − |
| Infusion 18/10 | 0 | | | |
| Post 19/10 | 1 | 20/10 | +++ | |
| Post (24/10) | 6 | 25/10 | +++ | |
| Post (31/10) | 13 | 3/11 | +++ | |

Example 12

Rat red cells were transformed in vitro according to the following method.

Normal rat plasma was used as the glycolipid diluent (although any other diluent can be used). For all experiments a 250 μg Le$^b$ per ml stock solution of glycolipid in plasma was prepared in 1 ml of plasma. Further dilutions of this stock solution in rat plasma were prepared as required.

Transformed red cells were prepared by adding an equal volume of plasma containing Lewis glycolipids (600 μl) to an equal volume of washed packed red cells (600 μl) and incubated as appropriate. At timed intervals, 75 μl of mixture was removed and any reactions stopped by washing the cells three times with saline and then suspended in saline. Cells were stored at 4° C. until serology was tested (against anti-Le$^b$) (Example E).

Example E

Serology of in vitro rat red cells transformed with different concentrations of Le$^b$ glycolipids for different lengths of time. Results are shown in Table 13.

TABLE 13

| Le$^b$ | Time incubated (hrs) | | | | | | | | |
|---|---|---|---|---|---|---|---|---|---|
| Conc | 0.5 | 1 | 2 | 4 | 8 | 12 | 24 | 36 | 48 |
| 25 | ++ | +++ | ++++ | ++++ | ++++ | ++++ | ++++ | ++++ | +++ |
| 12.5 | ++ | ++ | ++++ | ++++ | ++++ | ++++ | ++++ | ++++ | ++ |
| 6.3 | + | ++ | +++ | +++ | ++++ | ++++ | ++++ | +++ | ++ |
| 3.2 | − | + | ++ | ++ | +++ | +++ | ++++ | ++ | + |
| 1.6 | − | − | + | + | ++ | ++ | ++ | + | − |
| 0.8 | − | − | − | − | + | + | + | − | − |
| 0.4 | − | − | − | − | − | − | − | − | − |
| 0 | − | − | − | − | − | − | − | − | − |

Concentration = μg Le$^b$/ml of rat plasma

Example 13

Temperature dynamics were determined by flow cytometry analysis.

For this experiment the sensitivity of the flow cytometry analysis was first assessed against cells sensitised during incubation at 37° C. for 3 hours with different concentrations of Le$^b$ glycolipids. It was found that the flow cytometry analysis was most reliable for detecting the cells transformed with high concentrations of glycolipids>100 μg/ml, which caused a serological score of 3+ or 4+ within the incubation period (results not shown). In accordance with these results, red cells were transformed with plasma containing 250 μg/ml (25 μg/tube) for periods of time up to 8 hours at three different temperatures, 4° C., 22° C. and 37° C. The results were assessed by flow cytometry analysis (see Examples F1 and F2).

Example F1

Figure 4:
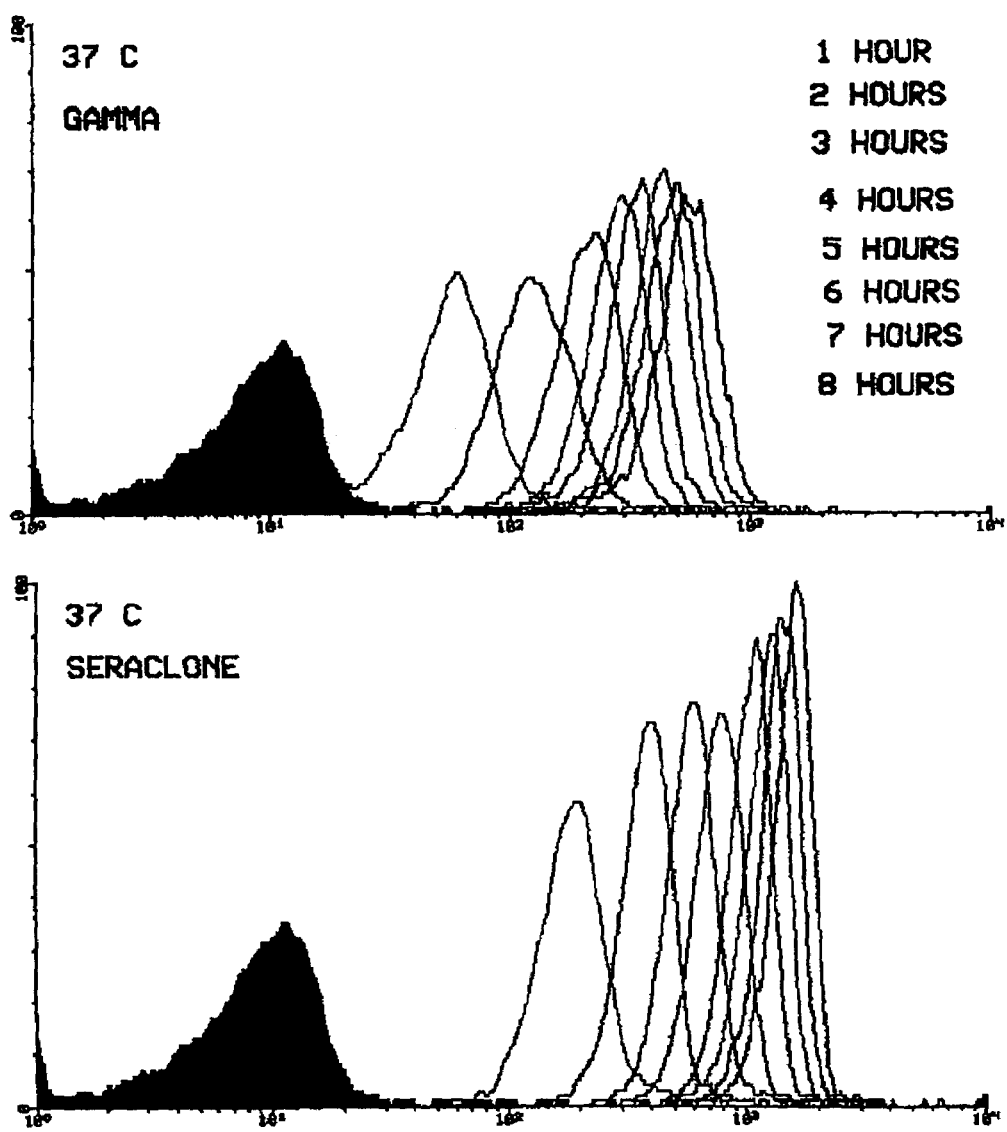
FIG. 4 shows the flow cytometry results of varying the time of in vitro transformation of red cells between 0 and 8 hours at 37° C. using two different anti-$Le^b$ primary reagents.

In vitro transformation of human Le(a−b−) red cells with Le$^b$ glycolipids over time at a transformation temperature of 37° C. Reactivity was determined by flow cytometry analysis using two different anti-Le$^b$ reagents. The results are shown in FIG. 4. The filled black curve represents the negative control, i.e. untransformed cells. The unfilled curves to the left represent the least amount of transforming time while those on the right represent the longer times. The results are in sequential order, i.e. from left to right being 0, 1, 2, 3, 4, 5, 6, 7, and 8 hours.

Example F2

Figure 5:
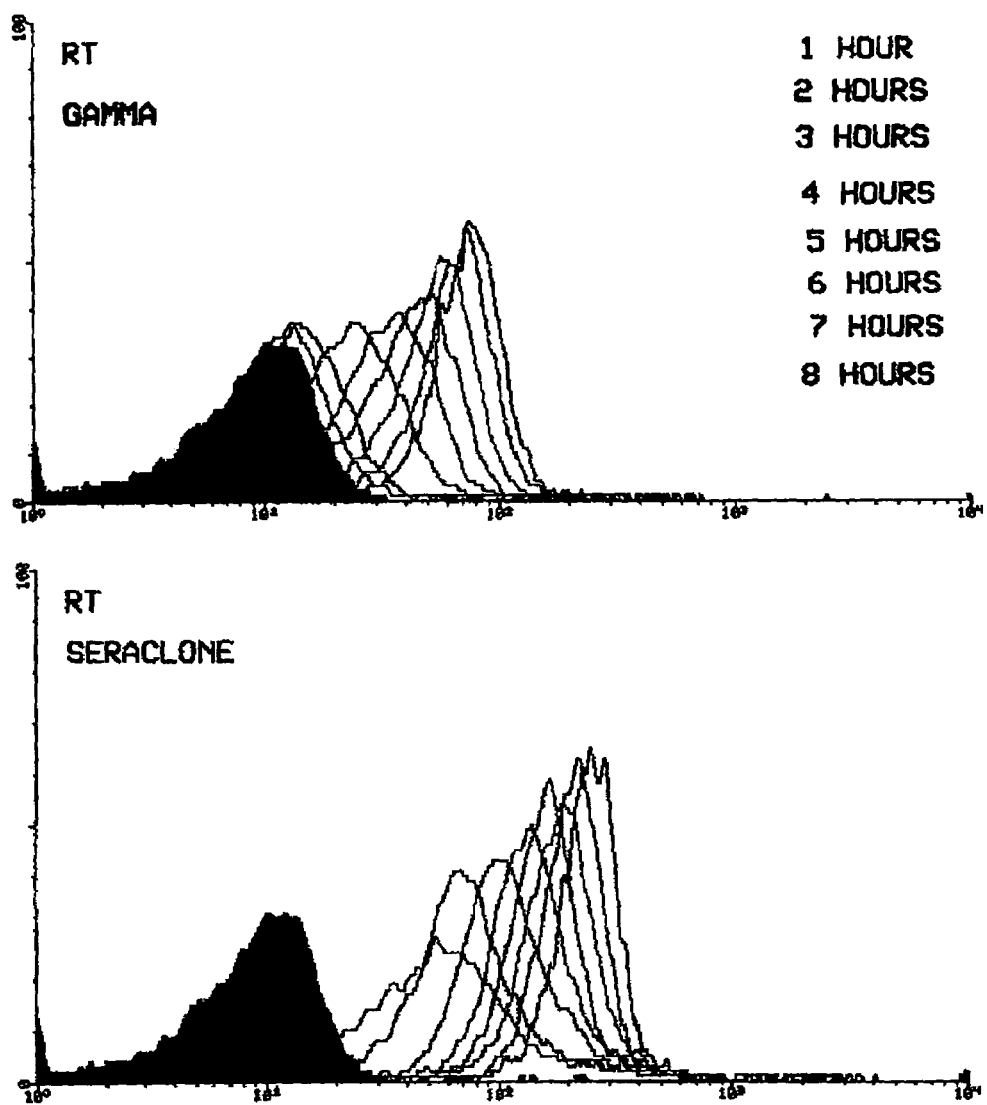
FIG. 5 shows the flow cytometry results of varying the time of in vitro transformation of red cells between 0 and 8 hours at 22° C. (RT) using two different anti-$Le^b$ primary reagents.

In vitro transformation of human Le(a−b−) red cells with Le$^b$ glycolipids over time at transformation temperature of 22° C. (RT). Reactivity was determined by flow cytometry analysis using two different anti-Le$^b$ reagents. The filled black curve represents the negative control, i.e. untransformed cells. The results are shown in FIG. 5. The unfilled curves to the left represent the least amount of transforming time while those on the right represent the longer times. The results are in sequential order, i.e. from left to right being 0, 1, 2, 3, 4, 5, 6, 7, and 8 hours.

Figure 6:
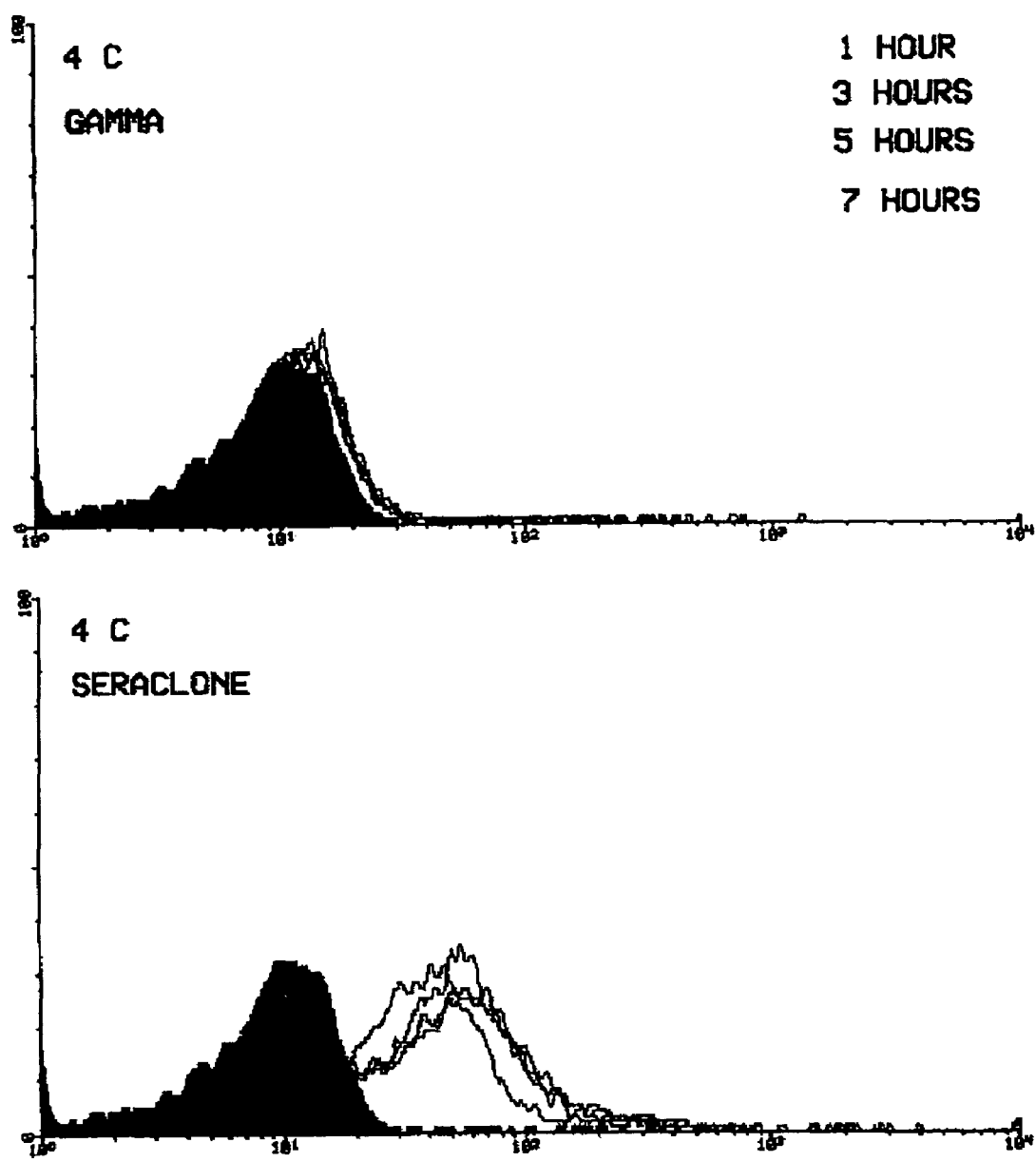
FIG. 6 shows the flow cytometry results of varying the time of in vitro transformation of red cells between 0 to 7 hours at 4° C. using two different anti-$Le^b$ primary reagents.

In vitro transformation of human Le(a−b−) red cells with Le$^b$ glycolipids over time at transformation temperature of 4° C. Reactivity was determined by flow cytometry analysis using two different anti-Le$^b$ reagents. The results are shown in FIG. 6. The filled black curve represents the negative control, i.e. untransformed cells. The unfilled curves to the left represent the least amount of transforming time while those on the right represent the longer times. The results are in sequential order, i.e. from left to right being 0, 1, 3, 5, and 7 hours.

Example 14

Dried glycolipid samples with PBS salts were prepared and reconstituted using the following methods:

Example G1

Glycolipid samples were prepared and dried as follows:
Dried glycolipid was dissolved in chloroform:methanol (2:1) to a concentration of 50 mg/ml.
Dissolved glycolipid (500 μl) was transferred to a glass tube. Working strength phosphate buffered saline (PBS 500 μl or alternatively 50 μl of 10×PBS) was then added. A small amount of methanol was also added to facilitate the formation of a single phase solution.
The solution was dried in a 70° C. heating block under nitrogen gas. During drying, the solution periodically separated out into two phases, and a small amount of methanol was added to return it to one phase to facilitate evaporation. The glycolipid sample could be fully dried in this way. Alternatively, the glycolipid sample can be frozen at minus 85° C. and freeze-dried.

Example G2

The dried glycolipid samples were redissolved as follows:
Deionised water (500 μl) was added to the dried glycolipid samples to produce a 50 mg/ml solution of glycolipid in PBS. The tube was sonicated for 2 min to ensure that the sample was completely dissolved. The sample could then be further diluted to desired concentrations with working strength PBS.

Example 15

This is an alternative and preferred method for the insertion of glycolipids into RBCs, which makes use of the 3:1 ratio:
Blood group A glycolipids (20 μl, 10 mg/ml) and washed packed group O RBCs (60 μl) were added to an eppendorf tube.
The tube was incubated in a 25° C. waterbath for four hours, with mixing every hour (RT is less stressful for the insertion step, as demonstrated by negligible haemolysis compared with incubations at 37° C.).
The transformed RBCs were washed 3× with PBS and then suspended in a cell preservative solution at a concentration suitable for serology.

Tube serology results from glycolipid insertion experiments at day 1 and after 25 and 62 days storage at 4° C. are shown in Table 14 below.

TABLE 14

Tube serology of transformed RBCs using anti-Le$^b$ (SCR A40-1-2/A40-1-1) and Seraclone anti-A (KIL 2901 E6-2/E6-3). Note: the Le$^b$ glycolipid sample had been HPLC purified, whereas the A glycolipid sample had not, and thus contained other lipid impurities.

| Glycolipid concentration | Le$^b$ | | | A | |
|---|---|---|---|---|---|
| (mg/mL) | Day 1 | Day 25 | Day 62 | Day 1 | Day 25 |
| 10 | ++++ | nd | ++/+++ | +++ | ++ |
| 5 | ++++ | nd | ++/+++ | ++ | ++ |
| 2 | +++ | nd | +/++ | 0 | + |
| 1 | ++++ | nd | ++ | 0 | + |
| 0.1 | +++ | ++ | 0 | 0 | nd |
| 0.01 | ++ | ++ | 0 | 0 | nd |
| 0.001 | ++ | ++ | 0 | 0 | nd |
| 0.0001 | ++ | 0 | 0 | 0 | nd |
| Control | 0 | 0 | 0 | 0 | 0 | nd = not determined

Example 16

Example H1

Cell agglutination was assessed using the Diamed-ID Micro Typing System in addition to using conventional tube serology. The cards used were NaCl, enzyme test and cold agglutinin cards, which are not pre-loaded with any antisera or other reagents. This allows the use of specific antisera.

Tables 15 and 16 below show the agglutination results obtained with this system.

TABLE 15

Diamed-ID Micro Typing System agglutination results for group O cells transformed 8 days previously with A glycolipid. The antibody used is a Seraclone anti-A (experiment KIL2202 E16-1).

| Lane/well | Transforming glycolipid mg/ml | Score |
|---|---|---|
| 188-1 | control | Negative—untreated O cells |
| 185-0 | 10 | +++ |
| 185-1 | 5 | +++ |
| 185-2 | 2 | ++ |
| 185-3 | 1 | 0 |
| 185-4 | 0.1 | 0 |

TABLE 16

Diamed-ID Micro Typing System agglutination results for group O cells transformed 17 days previously with A glycolipid. The antibody used is a Seraclone anti-A (experiment KIL2202 E41-2).

| Lane/well | Transforming glycolipid mg/ml | Score |
|---|---|---|
| 8-1 | control | ++++ |
| 185-0 | 10 | +++ |
| 185-1 | 5 | ++ |
| 185-2 | 2 | 0 |
| 185-3 | 1 | 0 |
| 190-1 | 0 | Negative—untreated O cells |

Example H2

A comparative trial was carried out using tube serology and the Diamed system to establish the comparative performance of the two systems. Seraclone and Alba-clone anti-A sera were used to establish whether their performance characteristics were equivalent between the two systems. The results are shown in Table 17 below.

TABLE 17

Agglutination results using two different anti-A sera—Seraclone and Albaclone. Cells and antisera were tested in tubes and in the Diamed system.

| | A glycolipid (mg/mL) | | | | |
|---|---|---|---|---|---|
| | 10 | 5 | 2 | 1 | 0 |
| | Tube | | | | |
| Seraclone | 3+ | 2+ | 0 | 0 | 0 |
| Alba-clone | 3+ | 2+ | 0 | 0 | 0 |
| | Diamed | | | | |
| Seraclone | 3+ | 2+ | 1+ | +w | 0 |
| Alba-clone | 2+ | 2+ | 0 | 0 | 0 |

Example 17

The stability of the glycolipid insertion was investigated according to the following method.

Two sets of cells were transformed with different concentrations of A glycolipid. One set was tested for agglutination at week 1 and 6, and the other was tested weekly. The agglutination results from tube serology and Diamed are shown in Table 18 below. The cells for weekly testing were divided between two cell storage solutions—CellStab and Celpresol—as a means of comparing their performance. All cells were stored in bottles with flat bases. No significant difference was seen between the two cell preservative solutions as judged by differences in agglutination scores or haemolysis. The cells showed minimal to no haemolysis at any time.

TABLE 18

Agglutination results for cells transformed with different concentrations of A glycolipid. Results from day 29 onwards were obtained using Alba clone anti-A, all others used Seraclone anti-A (see Table 17 above for equivalence data for these two antisera).

| | | 10 | 5 | 2 | 1 | 0.1 | control |
|---|---|---|---|---|---|---|---|
| | | Long term testing | | | | | |
| Day 1 | Tube | 4+ | 3+ | 2+ | 1+ | +w | 0 |
| | Diamed | 3+ | 3+ | +w | 0 | 0 | 0 |
| Day 17 | Tube | 3+ | 2+ | 0 | 0 | nd | 0 |
| | Diamed | 3+ | 2+ | 1+ | 0 | nd | 0 |
| | | Weekly testing | | | | | |
| Day 1 | Tube | 3+ | nd | 2+ | nd | 0 | 0 |
| | Diamed | 3+ | nd | 0 | nd | 0 | 0 |
| Day 8 | Tube | 1+ | nd | 0 | nd | 0 | 0 |
| | Diamed | 3+ | nd | 0 | nd | 0 | 0 |
| Day 15 | Tube | 1+ | nd | 0 | nd | 0 | 0 |
| | Diamed | 3+ | nd | 2+ | nd | 0 | 0 |
| Day 22 | Tube | 3+ | nd | 0 | nd | 0 | 0 |
| | Diamed | 3+ | nd | 0 | nd | 0 | 0 |
| Day 29 | Tube | 1+.w | nd | 0 | nd | 2+ | 0 |
| | Diamed | 4+ | nd | 3+ | nd | 0 | 0 |
| Day 36 | Tube | 4+ | nd | 2+ | nd | 0 | 0 |
| | Diamed | 4+ | nd | 3+ | nd | 0 | 0 |
| Day 43 | Tube | 4+ | nd | 3+ | nd | 0 | 0 |
| | Diamed | 3+ | nd | 0 | nd | 0 | 0 |
| Day 49 | Tube | 1+ | nd | nd | nd | nd | 0 |
| | Diamed | 3+ | nd | nd | nd | nd | 0 |
| Day 57 | Tube | 2+ | nd | nd | nd | nd | 0 |
| | Diamed | 2+ | nd | nd | nd | nd | 0 |

Example 19

Preparation of Biotinylated Gangliosides (BioG).
Biotinylated gangliosides (BioG) were prepared using a modified procedure described by Wilchek and Bayer (1987):
Dried gangliosides purified from porcine brains, were reconstituted in PBS with the aid of sonication.
The ganglioside sialic residues were oxidized by the addition of sodium m-periodate.
The solution was subjected to 24 hr dialysis to remove the resulting peroxide.
The oxidised ganglioside was incubated with biotin amidocaproyl hydrazide (Sigma B-3770) for 1 hr.
The solution was subjected to further overnight dialysis in water to remove excess biotin amidocaproyl hydrazide.
The resulting solution was dried via rotary evaporation and reconstituted in 50% methanol water. Further evaporation was performed under nitrogen gas in a reduced pressure desiccator overnight.
BioG samples (50 mg/ml) were diluted to the desired concentration in working strength PBS.

Preparation of Avidin.
Avidin is dissolved in working strength PBS to a concentration of 1 mg/ml.

Preparation of Biotinylated Saccharides.
Freeze-dried biotinylated saccharides were obtained from Syntesome.
A-PAA-biotin=Syntesome Cat No 165-BP
B-PAA-biotin=Syntesome Cat No 186-BP
They were resuspended to 1 mg/ml with deionised water, and diluted to the desired concentration with PBS.

Transformation Method
The synthetic transformation system occurs in three sequential stages. The first is the insertion of the biotinylated gangliosides (BioG) into the RBC membrane, followed by the conjugation of avidin (Av) onto the biotin of the ganglioside, and finishing with the conjugation of a biotinylated saccharide (eg A-PAA or B-PAA) onto the avidin molecule. All initial experiments were conducted with A-PAA.

Biotinylated Ganglioside Insertion.
BioG (20 µl, 0.01 mg/ml for cells intended for A-PAA conjugation) and washed packed group O RBCs (60 µl) were added to an eppendorf tube.
The tube was incubated in a 25° C. waterbath for four hours, with mixing every hour (RT was found to less stressful for the insertion step, as demonstrated by negligible haemolysis compared with incubations at 37° C.).
The transformed RBCs were washed 3× with PBS.

Avidin Conjugation.
Avidin (40 µL, 1 mg/ml) was added to the eppendorf tube containing the washed BioG RBCs (approximately 60 µL of red cells).
The tube was incubated at RT for 30 min, with mixing being carried out every 10 min.
The Av-BioG RBCs were washed 3× with PBS.

Biotinylated Saccharide Conjugation.
Biotinylated saccharides (60 µl, 0.001 mg/mL) were added to the eppendorf tube containing the washed Av-BioG RBCs (approximately 60 µl of red cells).
The tube was incubated at RT for 30 min, with mixing being carried out every 10 min.

The BioG-Av-A-PM RBCs were washed 3× with PBS, and suspended in Celpresol to a concentration of 5% for serology testing.

Example 20

A block titre was carried out to determine the minimum concentrations of both BioG and A-PAA required to generate RBCs that produce positive agglutination when tested against anti-A. The results are shown in Tables 19 and 20 below.

TABLE 19

Block Titre Results for A-PAA saccharide using a Seraclone anti-A.

| BioG concentration (mg/mL) | Bio-A-PAA concentration (mg/mL) | | | | | |
| --- | --- | --- | --- | --- | --- | --- |
| | 0.01 | 0.005 | 0.0025 | 0.0012 | 0.0006 | 0 |
| 0.03 | ++++ | ++++ | +++ | ++ | + | 0 |
| 0.02 | ++++ | ++++ | +++ | ++ | ++ | 0 |
| 0.01 | +++ | +++ | ++ | + | ++ | 0 |

TABLE 20

Block titre results for A-PAA saccharide with higher BioG concentrations, showing negative results for cells missing either the BioG or the A-PAA saccharide, or both. The anti-A used was Seraclone.

| BioG concentration (mg/mL) | Bio-A-PAA concentration (mg/mL) | | | | | |
| --- | --- | --- | --- | --- | --- | --- |
| | 0.01 | 0.005 | 0.0025 | 0.0012 | 0.0006 | 0 |
| 6 | ++++ | ++++ | ++ | + | (+) | (+) |
| 3 | ++++ | ++++ | ++ | +w | (+) | (+) |
| 1.5 | ++++ | ++++ | ++ | vw | 0 | 0 |
| 0.75 | ++++ | +++ | ++ | vw | 0 | 0 |
| 0.4 | ++++ | +++ | ++ | 0 | 0 | 0 |
| 0 | 0 | 0 | 0 | 0 | 0 | 0 |

Example 21

The stability of the BioG concentrations were analysed by the following methods. Cells were prepared using BioG concentrations of 0.5 mg/ml, 0.25 mg/ml, 0.12 mg/ml and 0.05 mg/ml with an A-PAA saccharide concentration of 0.01 and 0.0025 mg/ml using the established method. The 0.01 mg/ml cells were then tested weekly for serological score. No haemolysis was seen during the experiment.

TABLE 21

Agglutination results for cells transformed with different concentrations of BioG and A-PAA. Results after day 1 were obtained using Albaclone anti-A, all others used Seraclone anti-A (see Table 6 below for equivalence data for these two antisera).

| | | BioG concentration (mg/mL) | | | | |
| --- | --- | --- | --- | --- | --- | --- |
| | | 0.5 | 0.25 | 0.12 | 0.05 | 0 |
| A-PAA 0.0025 mg/mL | | | | | | |
| Day 1 | Tube | 1+ | 1+ | 2+ | 2+ | 0 |
| | Diamed | 2+ | 2+ | 2+ | 2+ | 0 |

TABLE 21-continued

Agglutination results for cells transformed with different concentrations of BioG and A-PAA. Results after day 1 were obtained using Albaclone anti-A, all others used Seraclone anti-A (see Table 6 below for equivalence data for these two antisera).

| | | BioG concentration (mg/mL) | | | | |
| --- | --- | --- | --- | --- | --- | --- |
| | | 0.5 | 0.25 | 0.12 | 0.05 | 0 |
| A-PAA 0.01 mg/mL | | | | | | |
| Day 1 | Tube | 4+ | 4+ | 4+ | 4+ | 0 |
| | Diamed | 4+ | 4+ | 4+ | 4+ | 0 |
| Day 8 | Tube | nd | nd | nd | nd | nd |
| | Diamed | 4+ | 4+ | 4+ | 4+ | 0 |
| Day 15 | Tube | 4+ | 4+ | 4+ | 4+ | 0 |
| | Diamed | 4+ | 4+ | 4+ | 4+ | 0 |
| Day 22 | Tube | 4+ | 4+ | 4+ | 4+ | 0 |
| | Diamed | 4+ | 4+ | 4+ | 4+ | 0 |
| Day 29 | Tube | 4+ | 4+ | 4+ | 4+ | 0 |
| | Diamed | 4+ | 4+ | 4+ | 4+ | 0 |
| Day 36 | Tube | 4+ | 4+ | 4+ | 4+ | 0 |
| | Diamed | 4+ | 4+ | 4+ | 4+ | 0 |
| Day 43 | Tube | 4+ | 4+ | 4+ | 2+ | 0 |
| | Diamed | 4+ | 4+ | 4+ | 4+ | 0 |
| Day 49 | Tube | 4+ | 4+ | 4+ | 2+ | 0 |
| | Diamed | 4+ | 4+ | 4+ | 4+ | 0 |
| Day 56 | Tube | 4+ | 4+ | 4+ | 3+ | 0 |
| | Diamed | 4+ | 4+ | 4+ | 3+ | 0 | nd—not determined.

A comparative trial was carried out using tube serology to establish whether Seraclone and Albaclone anti-A sera were equivalent. The cells were transformed with the concentrations of BioG shown and A-PAA saccharide 0.01 mg/ml.

TABLE 22

Agglutination results using two different anti-A sera—Seraclone and Albaclone. Cells and antisera were tested in tubes only.

| | BioG concentration (mg/mL) | | | | |
| --- | --- | --- | --- | --- | --- |
| A antisera | 0.5 | 0.25 | 0.12 | 0.05 | 0 |
| Seraclone | 4+ | 4+ | 4+ | 4+ | 0 |
| Albaclone | 4+ | 4+ | 4+ | 4+ | 0 |

Example 22

A trial of several expired antisera was carried out on cells transformed with 0.5 mg/ml, 0.25 mg/ml, 0.12 mg/ml and 0.05 mg/ml of BioG in block titre combination with 10 μg/ml, 7.5 μg/ml and 5 μg/ml of A-PAA. The antisera used are shown in Table 23 and results are given in Table 24.

TABLE 23

A antisera used in the comparative trial against cells synthetically transformed with the BioG-Av-B-PAA system.

| | | A Antisera | | |
| --- | --- | --- | --- | --- |
| Ref | Manufacturer | | Batch number | Expiry date |
| I | Albaclone, SNBTS | | Z0010680 | 1.2.03 |
| II | Bioclone | | 01102 | — |
| III | Bio Labs | | 8606 | 4.87 |

TABLE 23-continued

A antisera used in the comparative trial against cells synthetically transformed with the BioG-Av-B-PAA system.

A Antisera

| Ref | Manufacturer | Batch number | Expiry date |
|---|---|---|---|
| IV | Epiclone, CSL | 20901 | 11.93 |
| V | Gamma Clone | AM30-1 | 19.7.93 |
| VI | Immucor | 1A6137A | 22.4.93 |
| VII | Lorne Labs | 60086D | 8.01 |
| VIII | Nova Clone | NA00503 | 8.5.93 |
| IX | Organon | 112Z15A | 19.12.93 |
| X | Seraclone | 132051 | 29.5.93 |

TABLE 24

Agglutination results of the A antisera comparative trial.

| BioG (mg/mL) | A-PAA (µg/mL) | I | II | III | IV | V | VI | VII | VIII | IX | X |
|---|---|---|---|---|---|---|---|---|---|---|---|
| 0.5 | 10 | 2+ | 1+ | 0 | +w | 0 | 0 | 0 | 0 | +w | 2+ |
|  | 7.5 | 3+ | 2+ | 1+ | 2+ | 2+ | 2+ | +w | 0 | 1+ | 4+ |
|  | 5 | 3+ | 3+ | 1+ | 1+ | 0 | 0 | 0 | +w | 2+ | 2+ |
| 0.25 | 10 | 4+ | 2+ | 0 | 0 | 0 | 0 | 0 | 0 | 0 | 4+ |
|  | 7.5 | 3+ | 2+ | 0 | 1+ | 0 | 0 | 0 | 0 | 1+ | 4+ |
|  | 5 | 4+ | 2+ | 0 | +w | 0 | 0 | 0 | 0 | +w | 4+ |
| 0.12 | 10 | 3+ | 1+ | 0 | 0 | 0 | 0 | 0 | 0 | +w | 2+ |
|  | 7.5 | 1+ | 1+ | 0 | 2+ | 0 | 0 | 0 | 0 | 0 | 3+ |
|  | 5 | +w | +w | 0 | 0 | 0 | 0 | 0 | 0 | 0 | +w |
| 0.05 | 10 | +w | 0 | 0 | 0 | 0 | 0 | 0 | 0 | 0 | 1+ |
|  | 7.5 | 2+ | +w | 0 | 0 | 0 | 0 | 0 | 0 | 0 | 2+ |
|  | 5 | +w | 0 | 0 | 0 | 0 | 0 | 0 | 0 | 0 | 1+ |
| Negative control |  | 0 | 0 | (+) | 0 | 0 | 0 | 0 | 0 | 0 | 0 |
| Positive control |  | 4+ | 4+ | 4+ | 4+ | 4+ | 4+ | 4+ | 4+ | 4+ | 4+ |

I—Albaclone,
II—Bioclone,
III—Bio Labs,
IV—CSL,
V—Gamma Clone,
VI—Immucor,
VII—Lorne Labs,
VIII—Nova Clone,
IX—Organon,
X—Seraclone.

Some of these antisera were tested in the Diamed system. Selected results are shown below in Tables 25, 26, and 27.

TABLE 25

Diamed-ID Micro Typing System agglutination results for group O cells transformed with the indicated concentrations of BioG and A-PAA. The antibody used is the Albaclone anti-A (experiment KIL2403 E93-1-1).

| Lane/well | Transforming BioG (mg/mL) and A-PAA (µg/mL) | Score |
|---|---|---|
| 04-2 | Positive control—group A cells | ++++ |
| 66-1-1 | 0.5 mg/mL BioG and 10 µg/mL A-PAA | ++ |
| 66-1-2 | 0.25 mg/mL BioG and 10 µg/mL A-PAA | +++ |
| 66-1-3 | 0.12 mg/mL BioG and 10 µg/mL A-PAA | ++ |
| 66-1-4 | 0.05 mg/mL BioG and 10 µg/mL A-PAA | 0 |
| 66-4 | Negative control—group O cells | 0 |

TABLE 26

Diamed-ID Micro Typing System agglutination results for group O cells transformed with the indicated concentrations of BioG and A-PAA. The antibody used is the Albaclone anti-A (experiment KIL2403 E93-1-2).

| Lane/well | Transforming BioG (mg/mL) and A-PAA (µg/mL) | Score |
|---|---|---|
| 04-2 | Positive control—group A cells | ++++ |
| 66-2-1 | 0.5 mg/mL BioG and 7.5 µg/mL A-PAA | ++++ |
| 66-2-2 | 0.25 mg/mL BioG and 7.5 µg/mL A-PAA | +++ |
| 66-2-3 | 0.12 mg/mL BioG and 7.5 µg/mL A-PAA | ++ |
| 66-2-4 | 0.05 mg/mL BioG and 7.5 µg/mL A-PAA | 0 |
| 66-4 | Negative control—group O cells | 0 |

TABLE 27

Diamed-ID Micro Typing System agglutination results for group O cells transformed with the indicated concentrations of BioG and A-PAA. The antibody used is the Seraclone anti-A (experiment KIL2403 E93-2-3).

| Lane/well | Transforming BioG (mg/mL) and A-PAA (µg/mL) | Score |
|---|---|---|
| 04-2 | Positive control—group A cells | ++++ |
| 66-3-1 | 0.5 mg/mL BioG and 5 µg/mL A-PAA | +++ |
| 66-3-2 | 0.25 mg/mL BioG and 5 µg/mL A-PAA | +++ |
| 66-3-3 | 0.12 mg/mL BioG and 5 µg/mL A-PAA | 0 |
| 66-3-4 | 0.05 mg/mL BioG and 5 µg/mL A-PAA | 0 |
| 66-4 | Negative control—group O cells | 0 |

O cells were synthetically transformed with a biotinylated B-trisaccharide with the PAA linker (B-PM). BioG concentrations used were 0.5 mg/ml, 0.25 mg/ml, 0.12 mg/ml and 0.05 mg/ml, and the B-PAA concentrations were 10 µg/ml, 7.5 µg/ml and 5 µg/ml as for the A-PM. The B antisera used are shown in Table 28, and the results of the trial are presented in Table 29.

TABLE 28

B antisera used in the comparative trial against cells synthetically transformed with the BioG-Av-B-PAA system.

| | B Antisera | | |
|---|---|---|---|
| Ref | Manufacturer | Batch number | Expiry date |
| I | Albaclone, SNBTS | Z0110600 | 27.4.03 |
| II | Bioclone | 01103 | — |
| III | Bio Labs | 8625 | 7.87 |
| IV | Epiclone, CSL | 23801 | 5.00 |
| V | Epiclone, CSL | 20801 | 11.93 |
| VI | Lorne Labs | 61003A | 8.01 |
| VII | Organon | 112X19B | 16.12.93 |
| VIII | Ortho Clinical Diagnostics | BBB589A | 21.11.99 |

TABLE 29

Agglutination results of the B antisera comparative trial.

| BioG (mg/ mL) | B-PAA (μg/mL) | B antisera I | II | III | IV | V | VI | VII | VIII |
|---|---|---|---|---|---|---|---|---|---|
| 0.5 | 10 | 2+ | 3+ | 1+ | +w | 0 | 2+ | 0 | 4+ |
| | 7.5 | 0 | 0 | 2+ | 0 | 0 | 0 | 0 | 0 |
| | 5 | 0 | 0 | 1+ | 0 | 0 | 0 | 0 | 2+ |
| 0.25 | 10 | 2+ | 2+ | 1+ | 0 | 0 | 3+ | 0 | 4+ |
| | 7.5 | 0 | 0 | 0 | 0 | 0 | 0 | 0 | 0 |
| | 5 | 0 | 0 | 1+ | 0 | 0 | 0 | 0 | 2+ |
| 0.12 | 10 | 0 | 0 | 0 | 0 | 0 | 0 | 0 | 2+ |
| | 7.5 | 0 | 0 | 0 | 0 | 0 | 0 | 0 | 1+ |
| | 5 | 0 | 0 | +w | 0 | 0 | 0 | 0 | 2+ |
| 0.05 | 10 | 0 | 0 | 0 | 0 | 0 | 0 | 0 | +w |
| | 7.5 | 0 | 0 | 0 | 0 | 0 | 0 | 0 | 0 |
| | 5 | 0 | 0 | 0 | 0 | 0 | 0 | 0 | +w |
| Negative control | | 0 | 0 | 0 | 0 | 0 | 0 | 0 | 0 |
| Positive control | | 4+ | 4+ | 4+ | 4+ | 4+ | 4+ | 4+ | 4+ |

I—Albaclone,
II—Bioclone,
III—Bio Labs,
IV & V—CSL,
VI—Lorne Labs,
VII—Ortho Clinical Diagnostics,
VIII—Organon.

Although the invention has been described by way of example, it should be appreciated that variations and modifications may be made without departing from the scope of the claims. Furthermore, where known equivalents exist to specific features, such equivalents are incorporated as if specifically referred in this specification.

The invention claimed is:

1. A sensitivity control composition comprising a suspension of modified red blood cells for use in blood group determination where the modified red blood cells are modified by insertion of group A or group B blood group antigen glycolipids, or a mixture thereof, in known concentrations into the membranes of group O red blood cells.

2. The composition according to claim 1 prepared by a process comprising:

contacting a solution of blood group-related antigen glycolipids of known concentration with a suspension of group O red blood cells of known concentration under conditions sufficient to allow insertion of said blood group-related antigen glycolipids into the group O red blood cell membranes to provide modified red blood cells;

washing the modified red blood cells with a washing solution; and then suspending the modified red blood cells;

where the solution of blood group-related antigen glycolipids is a solution comprising group A or group B blood group antigen glycolipids or a mixture thereof.

3. The composition according to claim 2, wherein the modified red blood cells are suspended in water.

4. The composition according to claim 2, wherein the modified red blood cells are suspended in water further comprising one or more dissolved salts.

5. The composition according to claim 4, wherein the blood group-related antigen glycolipid is a glycosphingolipid.

6. The composition according to claim 1, 2, 3, 4 or 5, wherein the modified red blood cells are human cells.

7. A kit comprising a sensitivity control composition according to claim 1, 2, 3, 4 or 5 and instructions for the use of said composition as a blood group determination sensitivity control.

8. A blood group determination sensitivity control kit, which comprises a sensitivity control composition according to claim 1, 2, 3, 4 or 5.

* * * * *